United States Patent
Keller

[11] Patent Number: 6,139,549
[45] Date of Patent: Oct. 31, 2000

[54] SPINAL FIXING DEVICE

[75] Inventor: Arnold Keller, Kayhude, Germany

[73] Assignee: Waldemar Link (GmbH & Co.), Hamburg, Germany

[21] Appl. No.: 09/254,290

[22] PCT Filed: Feb. 25, 1997

[86] PCT No.: PCT/EP97/00900

§ 371 Date: Mar. 3, 1999

§ 102(e) Date: Mar. 3, 1999

[87] PCT Pub. No.: WO97/37604

PCT Pub. Date: Oct. 16, 1997

[30] Foreign Application Priority Data

Apr. 9, 1996 [DE] Germany ......................... 296 06 468 U

[51] Int. Cl.$^7$ .................................................. A61B 17/58
[52] U.S. Cl. ................................ 606/61; 606/73; 606/104
[58] Field of Search ................................. 606/61, 72, 73, 606/104

[56] References Cited

U.S. PATENT DOCUMENTS 5,702,393  12/1997  Pfaifer ........................................ 606/61
5,928,233   7/1999  Apfelbaum et al. ....................... 606/61

FOREIGN PATENT DOCUMENTS 2 624 720   6/1989  France .
2 640 492   6/1990  France .
2 706 761  12/1994  France .
41 07 480 A1  9/1992  Germany .

*Primary Examiner*—Michael Buiz
*Assistant Examiner*—Julian W. Woo
*Attorney, Agent, or Firm*—Morrison & Foerster LLP

[57] ABSTRACT

Fixator for vertebra or bone fragments, with a rod and at least one pedicle screw which is to be secured thereon. The U-shaped head of the pedicle screw forms a receiving seat for the rod, which receives a fixing device for fixing the rod. The fixing device comprises a U-shaped clamping yoke whose legs can be connected with positive fit to the head of the pedicle screw and whose bridge holds a fixing screw. By means of the fixing screw, a U-shaped fixing yoke can be clamped with the ends of its legs against the rod, to the sides of the clamping yoke.

12 Claims, 5 Drawing Sheets

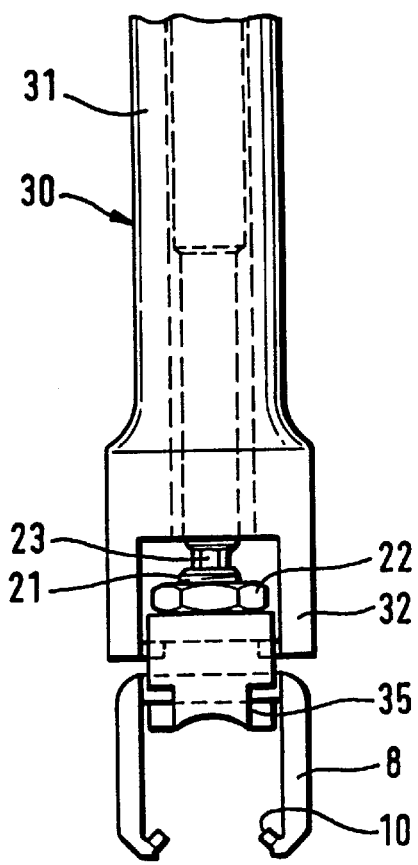
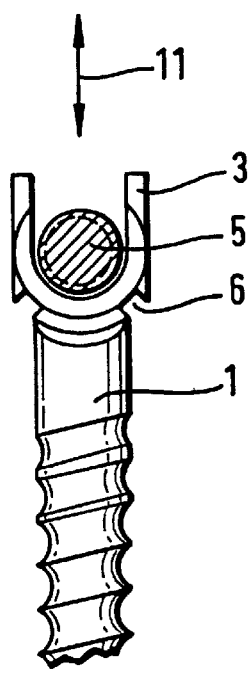
Fig. 2
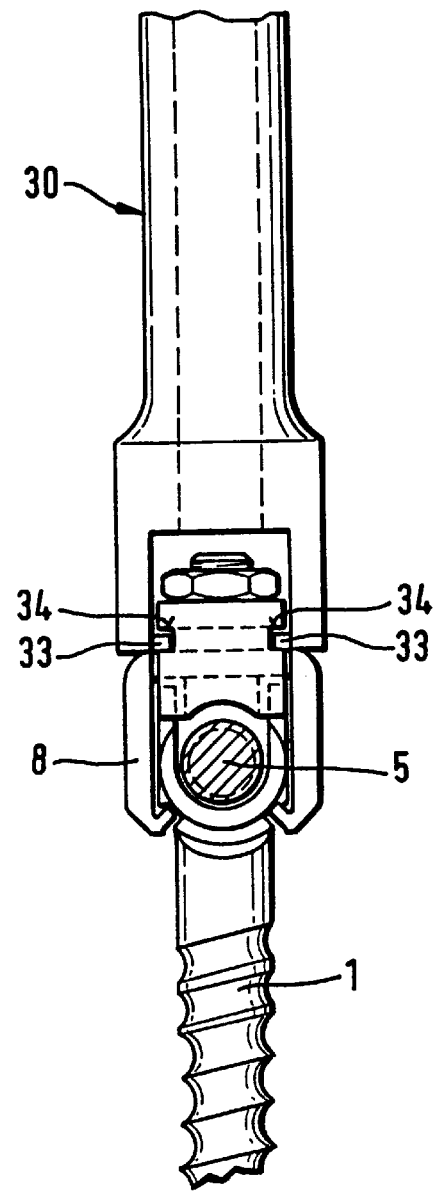
Fig. 3

SPINAL FIXING DEVICE

BACKGROUND OF THE INVENTION

The invention relates to a fixator for vertebrae or bone fragments, comprising a rod on which at least one pedicle screw is to be secured. The U-shaped head of the pedicle screw forms a receiving seat for the rod. The rod is held in the receiving seat by a fixing device which comprises a U-shaped clamping yoke whose legs can be connected with positive fit to the head of the pedicle screw and whose bridge holds a fixing screw. In a known spinal column fixator (DE-C 41 07 480) the fixing screw acts directly on the rod lying in the receiving seat. This has the disadvantage that the alternating forces which occur between rod and pedicle screw also act on the screw and may loosen it. This is particularly the case when the direction of the rod does not run exactly perpendicular to the longitudinal direction of the screw, and, as a result, a state of considerable looseness can arise upon relative movements, even when the screw has not moved.

The invention is therefore based on the object of making available a fixator of the type mentioned at the outset, which affords more secure connection between rod and pedicle screw and better mutual alignment to the perpendicular setting.

SUMMARY OF THE INVENTION

The solution according to the invention lies in the fact that the fixing screw does not act directly, or not exclusively directly, on the rod, and is instead used to clamp a U-shaped fixing yoke against the rod, with the ends of its legs to the sides of the clamping yoke.

The ends of the legs of the fixing yoke sit on the rod at a specific distance from the center of the fixing device and thus make it possible to exert a substantial restoring moment on this rod if it does not lie perpendicular in relation to the pedicle screw at the start of the fixing procedure. The perpendicular setting is therefore obtained very reliably during the course of the fixing procedure. This setting is also maintained very reliably under alternating forces. Relative movements between rod and fixing screw and within the fixing device do not in practice occur. Thus, the fixing screw is not acted upon by forces from alternating directions which may lead to its loosening. Rather, it is almost exclusively axial forces that act on the fixing screw.

Although the risk of loosening of the fixing screw is therefore considerably less than in the known solution, it can, in an advantageous embodiment of the invention, be provided with a securing device, in particular a locking nut. However, other known securing devices for these purposes can also be used.

In the known arrangement described at the outset, the interacting means on the head of the pedicle screw and on the clamping yoke, providing the positive fit, are designed as mutually engaging ribs and grooves running perpendicular to the direction of the pedicle screw and parallel to the rod. When, during the operation, the head of the pedicle screw is to be connected to the rod, it is often the case that these parts do not at the outset have the setting which they are intended to have; they first have to be adjusted in relation to each other by applying a certain force. Under these circumstances it can be difficult to align the fixing device with sufficient precision so that it can be pushed onto the head of the pedicle screw. The invention makes this procedure easier by making available an instrument for holding the fixing device in the correct direction. The instrument, which is equipped with a large hand grip, can be aligned easily in the desired manner, as a result of which the correct alignment of the fixing device is then also ensured. So that the fixing device is correctly aligned in relation to the instrument, according to the invention the instrument has a saddle-shaped holder part which has two rib-shaped projections which are located opposite one another and which engage under the edges of the bridge of the fixing yoke. The edges of the fixing yoke are in this way aligned with the direction of the ribs and thus also the direction of the instrument.

To ensure that the fixing device cannot be detached unintentionally from the instrument, the arrangement is set up in such a way that the rib-shaped projections of the instrument are clamped between the edges of the fixing yoke and the facing surface of the clamping yoke, by means of the fixing screw being tightened after insertion of the fixing device. The distance between the clamping yoke and the fixing yoke, as defined by the rib-shaped projections, should in this case be greater than the distance between these parts in the fixing state. The fixing yoke is thus still slightly raised in relation to the rod, and there is sufficient play present to push the fixing device onto the head of the pedicle screw, even when the rod is already located in the receiving seat of the pedicle screw. This arrangement, in which the fixing device is secured tightly on the instrument, by means of the ribs of the instrument being clamped between fixing yoke and clamping yoke, has the advantage that the fixing device sits on the instrument without any shaking. This facilitates application to the head of the pedicle screw. It requires, however, that the instrument be removed before the fixing device is tightened on the pedicle head, because the fixing state cannot be obtained as long as the fixing device is located on the instrument. In many cases this is not a problem, because the most difficult part of the manipulation is pushing the fixing device onto the head of the pedicle screw, and the subsequent tightening does not offer any particular problems.

The method can be simplified, however, if the mounting of the fixing device on the instrument is designed such that the fixing device can be tightened on the pedicle screw while it is still held in the instrument. For this purpose, the distance existing in the fixing state between the bridges of the fixing yoke and of the clamping yoke is of greater dimension than the height of the ribs holding the fixing device on the instrument. The instrument can therefore be detached from the fixing device even when the latter is clamped tight on the pedicle screw. This takes into consideration the fact that the fixing device cannot be braced on the instrument by drawing together the two yokes. However, fixing on the instrument can be achieved by means of the fact that the instrument and a screwdriver for manoeuvring the fixing screw are connected in such a way that the screwdriver applied to the screw head at the same time forms an obstacle to the withdrawal of the fixing device from the instrument.

In any event, it has proven expedient for the instrument to have a grip shaft which is designed as a guide for a screwdriver cooperating with the fixing screw. The simple insertion of the screwdriver into the guide ensures that the screwdriver readily finds the position in which it engages in the fixing screw. In this position, it locks the fixing device securely against a movement whose direction runs transverse to the direction of the screwdriver and thus secures it on the instrument.

It is not only pushing the fixing device onto the head of the pedicle screw that can prove difficult under operating conditions, but also subsequently finding the correct centring position of the fixing device relative to the pedicle screw. According to the invention, this can be made easier by the fact that the head of the pedicle screw and the fixing device have an interacting pair of limit stops delimiting the position of the fixing device in the correct position relative to the head of the pedicle screw in one direction. When the fixing device is pushed onto the screw head, the correct position thus results automatically.

The same principle can be used to facilitate the insertion of the fixing device into the instrument.

BRIEF DESCRIPTION OF THE DRAWINGS

The invention is discussed in greater detail hereinbelow with reference to the drawings in which:

FIG. 2 shows, in the rod direction, a view of the pedicle screw and of the fixing device held in an instrument.

FIG. 3 shows a side view, corresponding to FIG. 2, and from the opposite direction, after connection to the pedicle screw.

DETAILED DESCRIPTION OF THE INVENTION

Figure 1:
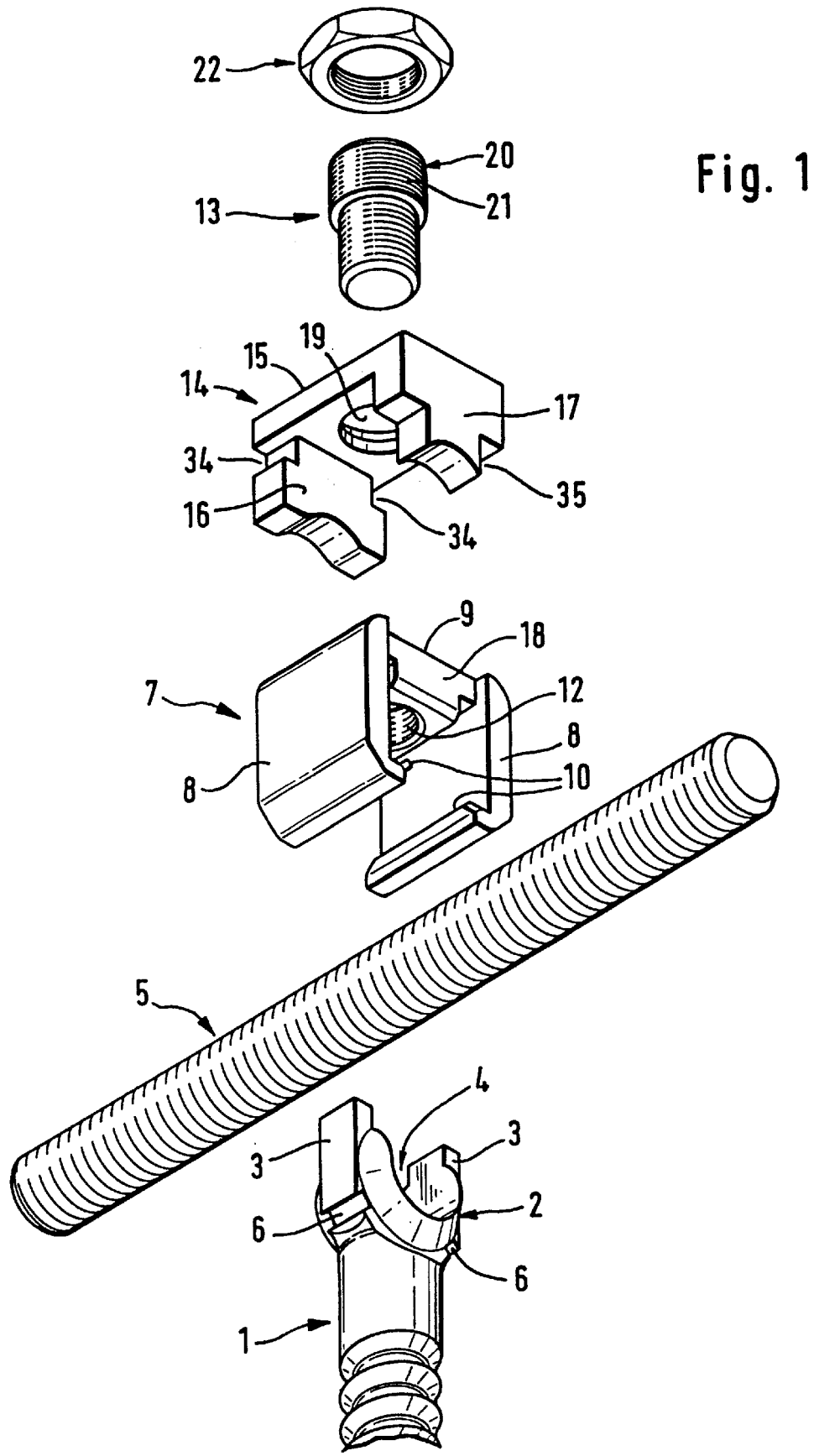
FIG. 1 shows an exploded view of the pedicle screw, the rod and the fixing device of this invention.
Figures 4, 5, 6:
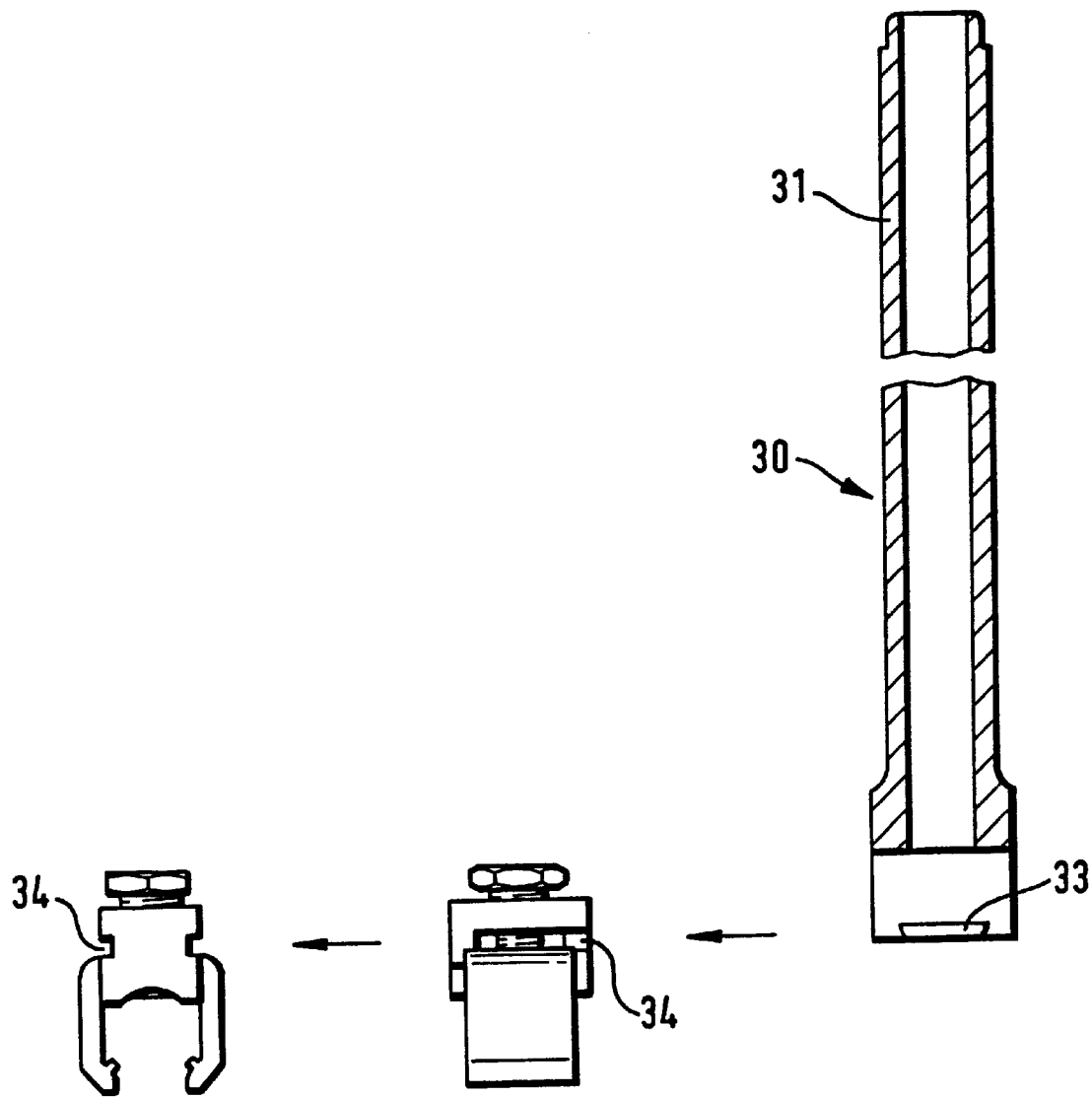
FIG. 4 shows a cross-sectional view of the instrument.
FIG. 5 shows a side view of the fixing device.
FIG. 6 shows a side view of the fixing device rotated 90 degrees relative to the view in FIG. 5.
Figures 7, 8:
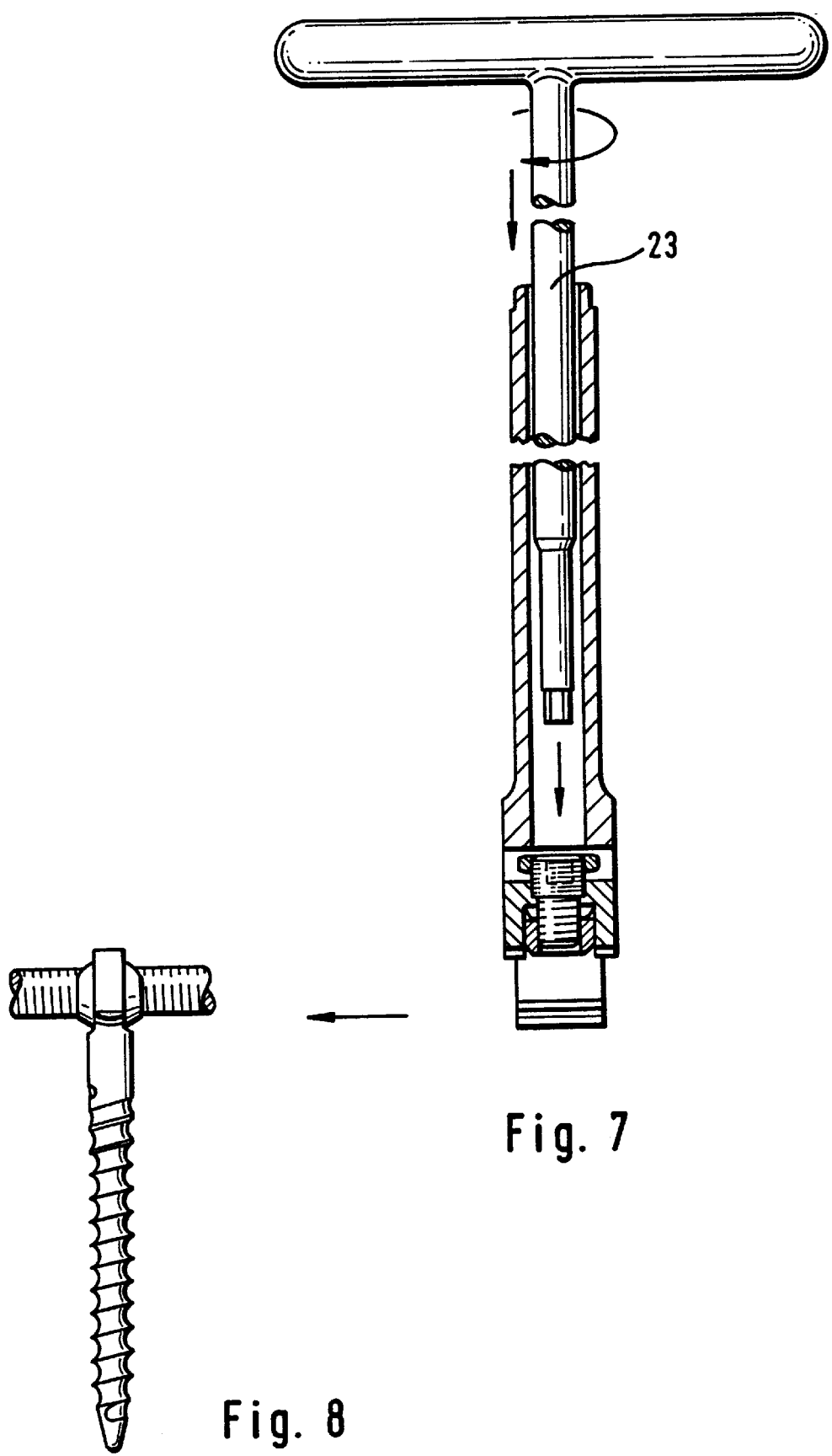
FIG. 7 shows a cross-section through the instrument with the fixing device held therein and the screwdriver.
FIG. 8 shows the pedicle screw with a rod fitted in its receiving seat, before the fixing device is applied.
Figure 9:
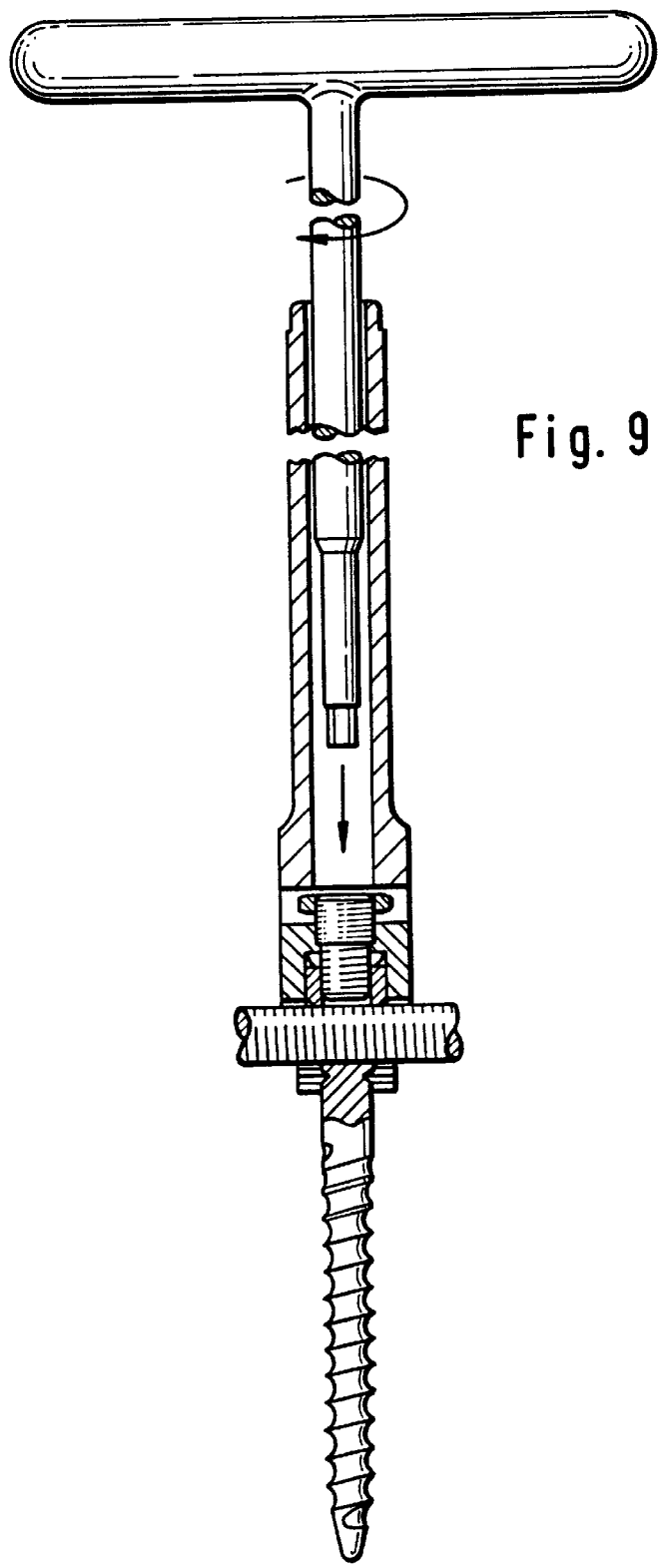
FIG. 9 shows the pedicle screw, rod, fixing device, instrument, and screw driver in the assembled state.

The pedicle screw 1 has a head 2 which is formed by two fork legs 3 which are shaped as a U and between which the receiving seat 4 for the rod 5 is situated. Near the ends of the legs 3 towards the shank there are grooves 6 which run perpendicular to the direction of the screw shank and parallel to the rod direction set by the receiving seat 4. The outer surfaces of the legs 3 are parallel to each other and to the plane defined by the longitudinal direction of the screw and the direction of the rod.

The clamping yoke 7, of a U shape, consists of two plate-like, mutually parallel legs 8 and of a bridge 9. The inside diameter between the legs 8 is equal to the width of the screw head between the outer surfaces of the legs 3. At their ends near the opening, the legs 8 are bent towards one another and in this area carry a rib 10 on each inner side, which rib 10 is designed matching the grooves 6 of the pedicle screw. The screw head can therefore be fitted into the space formed between the legs 8 and the bridge 9 of the fixing yoke, as is depicted in FIG. 3. It will be observed that the flanks of the ribs 10 and of the grooves 6 are inclined in such a way that they hold the two parts together with positive fit when they are being pulled apart by forces directed in the direction of the arrow 11 (FIG. 2).

The bridge 9 of the clamping yoke 7 has at its center a threaded bore 12 in which a fixing screw 13 fits. The latter serves to clamp the fixing yoke 14 onto the clamping yoke 7. The fixing yoke 14 consists of a bridge 15 and two legs 16, 17, whose width corresponds, with slight play, to the inside diameter between the legs 8 of the clamping yoke 7.

The end faces 18 of the bridge 9 of the clamping yoke 7 are set back a little in relation to the edges of the legs 8. The inside diameter between the legs 16, 17 of the fixing clamp 14 is smaller than the width of the legs 8 and greater than that of the bridge 9 of the clamping yoke 7. When the fixing clamp 14 is placed on the clamping yoke 7, the legs 16, 17 of the fixing yoke are therefore guided between the legs 8 of the clamping yoke. The bridge 15 of the fixing yoke includes at its center a through-bore 19 for the fixing screw 13, whose head 20 sits on the upper side of the bridge 15 or in a corresponding depression therein when the parts are drawn together. The head 20 of the fixing screw 13 is provided with an external thread 21 matching a locking nut 22 which serves to secure the fixing screw in the mounted state. The fixing screw 13 includes in the head 20 a hexagonal recess for the engagement of a screwdriver 23.

Figure 10:
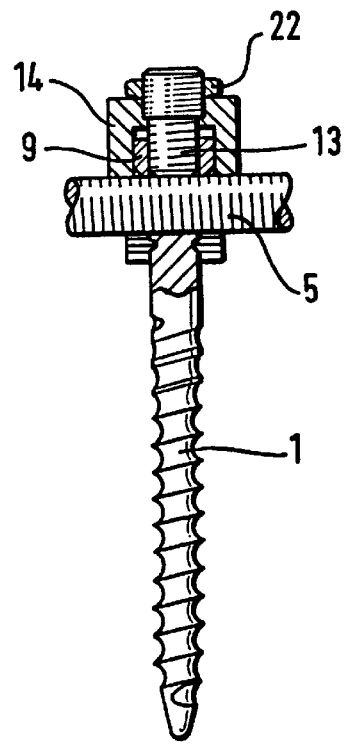
FIG. 10 shows the pedicle screw, the rod and the fixing device in the final mounted state.

When the parts shown in FIG. 2 have been assembled completely, the configuration shown in FIG. 10 is obtained. The rod 5 lies in the receiving seat 4 of the pedicle screw. The clamping yoke 7, of which only a part of the bridge 9 is visible in FIG. 10, is pushed over the head of the pedicle screw and is connected to the latter with positive fit via the ribs 10 and grooves 6. The fixing yoke 14 is braced by means of the fixing screw 13 in such a way that the ends of its legs 16, 17 sit on the rod 5. It is thus secured and is aligned at right angles to the pedicle screw 1. The end of the fixing screw 13 can sit on the rod 5 in addition to the ends of the legs 16, 17 of the fixing clamp; however, this is not normally desired. The fixing screw 13 is secured in its position by the locking nut 22.

In order to obtain this arrangement, the fixing device consisting of the yokes 7, 14, the screw 13 and locking nut 22 must be pushed over the head of the pedicle screw 1 after the rod 5 has assumed its position in the receiving seat 4. This is done by means of the instrument 30 which has a sturdy and easy to handle grip rod 31 and, at the end thereof, forms a saddle-shaped or fork-shaped mounting 32 for the fixing device. The mounting 32 has an inside diameter which is equal, with play, to the width of the bridge 15 of the fixing yoke 14 and has at the lower end two ribs 33 which face one another and via which it is pushed under the edges of the bridge 15 of the fixing plate. To make this possible, the leg 16 adjoining the bridge 15 has cutouts 34 which correspond to the cross-sectional size of the ribs 33. The leg 17 does not have any cutouts of this kind. When the instrument is pushed with its mounting 32 onto the bridge 15 of the fixing yoke, its end position is therefore determined by the ends of the ribs 33 abutting on the leg 17. These parts form a limit stop which determines the secure positioning of the fixing device in the mounting 32 of the instrument 30. In this position, the fixing device can be locked on the instrument in a manner described in detail hereinbelow.

Instrument and fixing device then together form an easy to handle unit, where the fixing device can be easily located in relation to the head 2 of the pedicle screw 1, onto which it is to be applied, by means of the instrument. Nor is there any difficulty in exerting pressure on the rod, by way of the instrument and via the fixing device, if the rod resists insertion into the receiving seat 4 of the pedicle screw.

So that the fixing device can be placed on the head 2 of the pedicle screw although the legs 3 of the pedicle screw extend over the entire inner height of the clamping yoke 7, the leg 17 of the fixing yoke has cutouts 35. The other leg 16 does not have any cutouts of this kind. The fixing device can therefore be placed on the pedicle screw only from one side and in one direction. The purpose of this arrangement is that a limit stop is formed by the leg 16 in cooperation with the screw head 2, by means of which limit stop the correct final position of the fixing device in relation to the screw head is determined.

When the fixing device has reached this position, the fixing screw 13 and the locking nut 22 are tightened.

There are two possible ways of holding the fixing device securely on the instrument 30 during assembly. The first of these possibilities is demonstrated in FIG. 3. The bridges 15 and 9 of the fixing yoke and clamping yoke 14 and 7, respectively, are drawn together by means of the screw 13 in such a way that the ribs 33 of the instrument 30 are clamped between the underside of the edges of the bridge 15 and the upper side of the bridge 9. This method of securing has the advantage that all the parts of the fixing device are connected rigidly to the instrument and the physician therefore has a very reliable sense of the position of the fixing device during fitting. A precondition for this is that in the state shown in FIG. 3, that is to say when the ribs 33 are clamped between the yokes, there is still sufficient play present below the ends of the legs 16, 17 in relation to the rod 5. Otherwise, the fixing device would not be able to be pushed onto the pedicle screw and the rod 5 situated in it. This has the disadvantage that the clamping yoke 14 cannot be braced against the rod 5 as long as the instrument 30 is connected to the fixing device. Instead, the latter first has to be removed before the fixing screw 13 is tightened.

The other possibility for locking the fixing device on the instrument 30 is demonstrated in FIG. 2. As has been described before, the instrument is connected to the fixing device in such a way that the ribs 33 lie under the edges of the bridge 15 of the fixing yoke 14. The removal of the fixing device from this position is prevented by the fact that the screwdriver 23, which is guided through a bore of the grip 31 of the instrument 30, engages in the hexagonal depression of the screw head 21. This locking position of the screwdriver 23 can be maintained either by means of the fact that the grips of the screwdriver and of the instrument are held together, and thus a corresponding force is exerted on the screwdriver, or a spring arrangement is provided between these parts, pressing the screwdriver 23 downwards in FIG. 2. This manner of securing the fixing device on the instrument dispenses with clamping the ribs 33 of the instrument between the two yokes, and the distance between the bridges 9 and 15 of the yokes can therefore be dimensioned so large that the ribs 33 are not even clamped when the fixing yoke 14 is braced against the rod 5. This procedure can therefore be effected while the instrument 30 is still connected to the fixing device. This not only has the advantage that a work stage is omitted, but also makes it easier to find the fixing screw 13 with the screwdriver 23 in the sometimes unclear operating field. This is because the screwdriver is by necessity guided through the bore in the instrument 30 to the screw head 21 and then finds itself in constant engagement therewith.

What is claimed is:

1. A fixator for vertebra or bone fragments, comprising:

(a) a rod;

(b) at least one pedicle screw having a U-shaped head formed as a receiving seat for the rod; and (c) a fixing device for fixing the rod in the receiving seat, comprising:

(i) a U-shaped clamping yoke having legs that can be connected to sides of the U-shaped head of the pedicle screw to provide a positive fit between said legs and said sides;

(ii) a U-shaped fixing yoke; and (iii) a fixing screw that serves to connect a bridge of the fixing yoke to a bridge of the clamping yoke.

2. A fixator for vertebra or bone fragments according to claim 1, further comprising a securing device for the fixing screw.

3. A fixator for vertebra or bone fragments according to claim 2, wherein the securing device is a locking nut.

4. A fixator for vertebra or bone fragments according to claim 1, comprising complementary ribs and grooves on the legs of the clamping yoke and the sides of the pedicle screw such that the clamping yoke can be pushed, relative to the longitudinal direction of the complementary ribs and grooves, onto the head of the pedicle screw.

5. A fixator for vertebra or bone fragments according to claim 4, wherein one or both of the legs of the fixing yoke has a cutout on each side of the leg adjoining the bridge of the fixing yoke.

6. A fixator for vertebra or bone fragments according to claim 5, further comprising an instrument for holding the fixing device, said instrument comprising a mounting at the end of the instrument having legs each with a rib-like projection that engages under edges of the bridge of the fixing yoke through the cutouts.

7. A fixator for vertebra or bone fragments according to claim 6, wherein (a) the rib-like projections of the instrument are clamped between the bridge of the fixing yoke and the bridge of the clamping yoke by means of the fixing screw; and (b) a distance between the bridge of the fixing yoke and the bridge of the clamping yoke when the rod is fixed in the receiving seat is less than the height of the rib-like projections.

8. A fixator for vertebra or bone fragments according to claim 6, wherein a distance between the bridge of the fixing yoke and the bridge of the clamping yoke when the rod is fixed in the receiving seat is greater than the height of the rib-like projections.

9. A fixator for vertebra or bone fragments according to claim 6, wherein the instrument has a grip shaft designed such that it serves as a guide for a screwdriver cooperating with the fixing screw.

10. A fixator for vertebra or bone fragments according to claim 9, wherein the grip shaft is hollow along its length creating a bore through which the screwdriver is guided.

11. A fixator for vertebra or bone fragments according to claim 4, wherein the fixing device and the head of the pedicle screw have an interacting pair of limit stops that delimit the position of the fixing device relative to the head of the pedicle screw in one direction.

12. A fixator for vertebra or bone fragments according to claim 6, wherein the fixing device and the mounting at the end of the instrument have an interacting pair of limit stops that delimit the position of the instrument relative to the fixing device in one direction.

* * * * *